US006342238B1

(12) United States Patent
Simonnet et al.

(10) Patent No.: US 6,342,238 B1
(45) Date of Patent: Jan. 29, 2002

(54) ORGANOGEL COMPRISING AN OXIDATION-SENSITIVE HYDROPHILIC COMPOUND, AND USES THEREOF, IN PARTICULAR COSMETIC USES

(75) Inventors: Jean-Thierry Simonnet, Paris; Sylvie Legret, Chatillon, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/655,855

(22) Filed: Sep. 6, 2000

(30) Foreign Application Priority Data

Sep. 6, 1999 (FR) ............................................. 99 11117

(51) Int. Cl.$^7$ ................................................. A61K 7/00
(52) U.S. Cl. ...................... 424/401; 424/450; 424/59; 424/62; 514/474; 514/844; 514/2; 264/4.1
(58) Field of Search ................................... 514/474, 844, 514/2; 424/401, 450, 62, 59; 264/4.1

(56) References Cited

U.S. PATENT DOCUMENTS

| | | | | |
|---|---|---|---|---|
| 4,695,450 A | * | 9/1987 | Bauer et al. .................... 424/22 |
| 5,071,640 A | * | 12/1991 | Vanlerberghe et al. ......... 424/63 |
| 5,364,553 A | * | 11/1994 | Cao ........................ 252/174.12 |
| 5,591,449 A | * | 1/1997 | Bollens et al. ................ 424/450 |
| 5,736,567 A | * | 4/1998 | Cantin et al. ................ 514/474 |
| 5,741,518 A | * | 4/1998 | Ribier et al. ................. 424/450 |

FOREIGN PATENT DOCUMENTS

| | | |
|---|---|---|
| EP | 0 217 105 | 4/1987 |
| EP | 0 641 557 A1 | 3/1995 |
| EP | 0 755 674 A1 | 1/1997 |
| EP | 0 839 520 A1 | 5/1998 |

* cited by examiner

*Primary Examiner*—Diana Dudash
*Assistant Examiner*—Gina C Yu
(74) *Attorney, Agent, or Firm*—Oblon, Spivak, McClelland, Maier & Neustadt, P.C.

(57) ABSTRACT

A composition in the form of an emulsion comprising an oily phase which is dispersed, with the aid of a surfactant system, in a glycerol phase containing an oxidation-sensitive hydrophilic compound and optionally comprising at least one glycol in addition to the glycerol, characterized in that the surfactant system contains at least one surfactant capable of forming a lamellar phase on contact with the glycerol phase and having a melting point of greater than or equal to 35° C. The composition obtained has the appearance of a gel in which the hydrophilic compound is stabilized with respect to oxidation, this stabilization also being achieved under aerobic conditions. The invention also relates to the use of the said composition in order to tone the skin and/or to smooth out wrinkles and fine lines on the skin and/or to combat the harmful effects of UV radiation and pollution and/or to depigment the skin.

30 Claims, No Drawings

ORGANOGEL COMPRISING AN OXIDATION-SENSITIVE HYDROPHILIC COMPOUND, AND USES THEREOF, IN PARTICULAR COSMETIC USES

BACKGROUND OF THE INVENTION

1. Field of the Invention

The present invention relates to an organogel containing an oxidation-sensitive hydrophilic compound, i.e., a composition in the form of an emulsion comprising an oily phase which is dispersed, with the aid of a specific surfactant system, in a glycerol phase containing this hydrophilic compound.

2. Description of the Background

It is known to introduce hydrophilic active agents into cosmetic and/or dermatological compositions in order to provide specific skin treatments.

For example, ascorbic acid (or vitamin C) is known to stimulate the synthesis of connective tissue and in particular of collagen, to reinforce the defenses of skin tissue against external attacking factors such as ultraviolet radiation and pollution, to compensate for vitamin E deficiency in the skin, to depigment the skin and to have a free-radical-scavenging function. These last two properties make vitamin C an excellent candidate as a cosmetic or dermatological active agent for combating or preventing ageing of the skin.

In addition, it is also known to introduce enzymes into cosmetic compositions, and in particular proteases and lipases, which are used for their proteolytic and lipolytic properties. These enzymes are desired in the cosmetics field for their smoothing and cleansing power and for their ability to remove dead cells from the skin.

Unfortunately, certain active agents, and in particular those mentioned above, are unstable on account of their sensitivity to external factors such as light, heat or the presence of oxygen either from the air or contained in water. Thus, ascorbic acid degrades over time in aqueous solutions, this also occurring under anaerobic conditions, in which it is liable to undergo a sequence of hydrolysis and oxidation reactions depending in particular on the pH of the composition and on the presence of metal ions acting as catalysts. This degradation is even faster under aerobic conditions.

This instability runs counter to the desired efficacy and can, furthermore, be a factor which users find unpleasant, for example when the instability of the active agent results in changes in the color and/or odor of the composition containing these agents.

Thus, various means have been envisaged to stabilize these active agents. For example, when the active agent comprises a reactive site, in particular in the case of ascorbic acid, one of the means for stabilizing it consists, for example, in blocking this site by esterification in particular with phosphate derivatives and in using these derivatives instead of the free active agent. Unfortunately, these derivatives are often less effective than the free active agent.

It has also been envisaged to use precursors of such active agents, such as ascorbic acid saccharide esters which, after application to the skin, are cleaved by the enzymes of the skin and then release the free active agent. However, the use of such derivatives does not always allow the active agent to be released rapidly or in sufficient amount at the surface of the skin.

It thus remains desirable to be able to use these active agents in their free, chemically unmodified active form. However, given the abovementioned problems of instability, the formulation of these active agents imposes very considerable constraints. It is thus necessary to formulate the ascorbic acid without heating, under an inert atmosphere and, above all, to store the products obtained in fully leaktight packaging.

A support, known as a hydrogel, comprises an oily phase which is dispersed, with the aid of a specific surfactant system, in a glycerol phase comprising an oxidation-sensitive hydrophilic compound, is capable of maintaining the activity of this active agent which is sensitive to oxygen in the air and/or in water, and thus of preventing its degradation.

The term "organogel" was initially used to describe a specific concept of gelation, by a gelatin solution, of a water-in-oil inverse microemulsion (see Luisi et al. Colloid & Polymer Science, 1990, vol. 268, p. 356–374). The term has recently been extended to gelled systems comprising two immiscible phases (water in oil) stabilized in lecithin enriched with phosphatidylcholine (referred to hereinbelow as PC) and usually hydrogenated (see Williman et al. Journal of Pharmaceutical Sciences, 1992, vol. 81, p. 871–874, and Schchipunov et al., Colloid Journal, 1995, vol. 57, p. 556–560). These emulsions have a lamellar phase and are in the form of gels even in the absence of gelling agents, hence the name organogels which denotes this type of emulsion irrespective of the orientation of the emulsion (W/O or O/W).

Thus, U.S. Pat. No. 5,639,740 discloses a lecithin organogel in the form of an oil-in-water emulsion, which is intended to promote the penetration of active agents such as salicylic acid, ceramides and α-hydroxy acids.

Similar emulsions have since been developed, in which the water is replaced with polygls, giving rise to the formation of oil-in-glycol emulsions, stabilized with hydrogenated lecithin. For various reasons, but in particular for reasons of cost, attempts have been made to replace the PC-enriched hydrogenated lecithin with other compounds in oil-in-polyol emulsions.

Thus, U.S. Pat. No. 5,587,149 describes emulsions comprising a first phase based on polyethylene glycol, optionally also comprising glycerol and/or water and in which is dissolved ascorbic acid, and a second phase based on silicone oil, liquid paraffins and/or plant oils. The emulsion also comprises a dispersant which may be a silicone surfactant or a polysorbate 20 or 80. Under certain conditions, polysorbate 80 is capable of forming lamellar phases. However, given the low melting point of this surfactant (<0° C.), these lamellar phases lack rigidity and result in a certain level of instability of the emulsion. In addition, stability of ascorbic acid is ensured only by the encapsulation of this emulsion in a gelatin capsule.

There is thus still a need for a composition in which oxidation-sensitive hydrophilic cosmetic active agents would conserve all their properties and thus their efficacy over time, and also achieving this under aerobic conditions, so as to reduce the formulation and packaging constraints on products containing these active agents and thus their cost price.

SUMMARY OF THE INVENTION

The Inventors have now discovered, unexpectedly, that a support, an organogel, comprising an oily phase which is dispersed, with the aid of a specific surfactant system, in a glycerol phase comprising an oxidation-sensitive hydrophilic compound, is capable of maintaining the activity of this active agent which is sensitive-to oxygen in the air and/or in water, and thus of preventing its degradation.

The Inventors have now discovered, surprisingly, that organogels of the oil-in-glycerol type emulsified with surfactants having a melting point of greater than or equal to 35° C. allow effective stabilization, which is also achieved in an aerobic medium, of ascorbic acid and other readily oxidizable hydrophilic compounds. These organogels thus support the introduction of relatively large amounts of water, e.g., up to 20% without harming the stability of the active agents they contain, thus allowing them to be formulated in the form of non-greasy fluids. However, they retain a water activity which is low enough to allow them to be formulated without preservative agents, thus making them particularly suitable for sensitive skin.

The present invention thus relates to a composition in the form of an emulsion comprising an oily phase which is dispersed, with the aid of a surfactant system, in a glycerol phase containing an oxidation-sensitive hydrophilic compound, characterized in that the surfactant system contains at least one surfactant capable of forming a lamellar phase on contact with the glycerol phase and having a melting point of greater than or equal to 35° C.

Accordingly, the present invention provides an emulsion, comprising:
 a glycerol phase containing an oxidation-sensitive hydrophilic compound;
 an oily phase dispersed in the glycerol phase; and
 at least one surfactant capable of forming a lamellar phase on contact with the glycerol phase and having a melting point of greater than or equal to 35° C.

A more complete appreciation of the invention and many of the attendant advantages. thereof will be readily obtained as the same becomes better understood by reference to the following detailed description.

DETAILED DESCRIPTION OF THE INVENTION

The hydrophilic compounds which are sensitive to oxidation by water and/or atmospheric oxygen and may be used according to the invention are, in particular, ascorbic acid and its hydrophilic derivatives, as well as enzymes. (Examples of enzyme include lactoperoxidase, lipase, protease, phospholipase, cellulase, catalase and superoxide dismutase).

The surfactants capable of forming a lamellar phase on contact with the glycerol phase, which are used in the composition of the invention, are amphiphilic and should not be soluble in water. They preferably have an HLB (hydrophilic-lipophilic balance) ranging from 1 to 10 and more preferably from 2 to 8. A single surfactant or a mixture of surfactants can be used. When a mixture of surfactants is used, the various surfactants constituting the mixture can have an HLB outside the range 1–10 provided that the mixture of nonionic surfactants has an HLB ranging from 1 to 10.

These surfactants are preferably selected from fatty esters of polyols, fatty ethers of polyols, mixtures of fatty esters of polyols and mixtures of fatty ethers of polyols. The esters are formed from at least one polyol and from at least one fatty acid. The fatty acid can contain from 8 to 22 carbon atoms and can have a saturated or unsaturated, linear or branched chain. Preferably, the fatty acid has a saturated and linear chain. This fatty acid is preferably selected from palmitic acid, stearic acid and mixtures thereof. The surfactants used in the composition of the invention can comprise from 1 to 10 fatty acid chains and preferably from 1 to 3 fatty acid chains.

The fatty ethers of polyols are formed from at least one polyol and from at least one fatty alcohol. The fatty alcohol can contain from 8 to 22 carbon atoms and can have a saturated or unsaturated, linear or branched chain. Preferably, the fatty alcohol has a saturated and linear chain. This fatty alcohol is preferably selected from cetyl alcohol, stearyl alcohol, lauryl alcohol and mixtures thereof.

The polyol constituting the surfactants used in the composition of the invention is preferably selected from the group formed by glycerol, polyglycerols, sorbitan, polysorbitans, polyoxyethylenated sorbitan derivatives and in particular those comprising from 1 to 20 ethylene oxide units, polyethylenes (PEG) and in particular those comprising from 1 to 40 ethylene oxide units, sucrose, glucose, oxyethylenated glucose derivatives and in particular those comprising from 1 to 20 ethylene oxide units, polyglucoses, oxyethylenated polyglucoses and in particular those comprising from 1 to 20 ethylene oxide units, and mixtures thereof.

The surfactants used in the present invention can be selected in particular from polyoxyethylenated derivatives of cetyl, stearyl and/or lauryl alcohol, esters of sorbitan and of stearic acid, esters of sorbitan and of palmitic acid, esters of sucrose and of stearic acid, esters of polyethylene glycol and of stearic acid, esters of glycerol or of polyglycerol and of stearic acid, and mixtures thereof.

By way of example, surfactants capable of forming a lamellar phase with the glycerol phase, include the following compounds (under the CTFA name, International Cosmetic Ingredient Dictionary and Handbook): ceteth-2 (for example Brij 52 sold by ICI), steareth-2 (for example Brij 72 sold by ICI), sorbitan palmitate (for example Span 40 sold by ICI), sorbitan stearate (for example Span 60 sold by ICI), sorbitan tristearate (for example Span 65 sold by ICI), PEG-8 stearate (for example Myij 45 sold by ICI), sucrose distearate which is a mixture of sucrose mono-, di- and triester (for example Crodesta F10, Crodesta F20 and Crodesta F50 sold by Croda), polyglyceryl-2 stearate (for example 10 Nikkol DGMS sold by Nikko), polyglyceryl-2 distearate (for example Emalex PSGA sold by Nikko) and polyglyceryl-3 distearate (for example Emalex DGS 3 sold by Nikko).

Another nonionic surfactant which can be used in the present invention is lecithin, preferably hydrogenated lecithin, enriched with phosphatidylcholine.

According to the invention, it is advantageous to add to the nonionic surfactant(s) at least one additive selected from the group formed by:
 sterols, and in particular phytosterols and cholesterol,
 long-chain alcohols and diols,
 long-chain amines and quaternary ammonium derivatives thereof.

Relative to the nonionic surfactant(s), the proportion of these additives will preferably not exceed 50% by weight.

In addition, the surfactant system of the composition according to the invention may comprise, instead of the nonionic surfactants mentioned above, one or more ionic surfactants. One ionic surfactant which is preferred in this case is lecithin enriched with phosphatidyltriethanolamine.

The combination of ionic and nonionic surfactants may also be useful, in certain cases, for improving the stability of the emulsion. Besides lecithin enriched with phosphatidyltriethanolamine, the ionic surfactants which can be used for this purpose may be selected from anionic surfactants which have preferably been neutralized, alkyl-sulphonic derivatives, cationic surfactants and mixtures thereof. However, the ionic surfactant should not modify the ability of the nonionic surfactant to form a lamellar phase. The anionic surfactants are selected more particularly from the group formed by:

dicetyl phosphate, dimyristyl phosphate and the alkaline salts thereof;

alkaline salts of cholesteryl sulfate;

alkaline salts of cholesteryl phosphate;

lipoamino acids such as mono- and disodium acylglutamates, for instance the disodium salt of N-stearoyl-L-glutamic acid sold under the name Acylglutamate HS21 by Ajinomoto;

the sodium salts of phosphatidic acid;

phospholipids.

The alkylsulphonic derivatives can be selected more particularly from alkylsulphonic derivatives of formula (I):

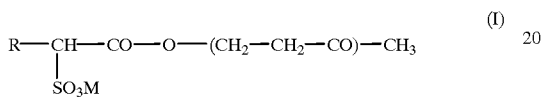

(I)

in which R represents an alkyl radical containing from 16 to 22 carbon atoms, in particular the $C_{16}H_{33}$ and $C_{18}H_{37}$ radicals taken as a mixture or separately, and M is an alkali metal, such as sodium.

The cationic surfactants can be selected, for example, from the group formed by quaternary ammonium salts and fatty amines and salts thereof.

The quaternary ammonium salts are, for example:

salts which have the general formula (II) below:

(II)

in which the radicals $R_1$ to $R_4$, which may be identical or different, represent a linear or branched aliphatic radical containing from 1 to 30 carbon atoms, or an aromatic radical such as aryl or alkylaryl. The aliphatic radicals can comprise hetero atoms such as, in particular, oxygen, nitrogen, sulphur or halogens.

The aliphatic radicals are selected, for example, from alkyl, alkoxy, polyoxy($C_2$–$C_6$)alkylene, alkylamide, ($C_{12}$–$C_{22}$) alkylamido($C_2$–$C_6$)alkyl, ($C_{12}$–$C_{22}$)alkyl acetate and hydroxyalkyl radicals containing from 1 to 30 carbon 10 atoms approximately; X is an anion selected from the group formed by halides, phosphates, acetates, lactates, ($C_2$–$C_6$)alkyl sulfates and alkyl or alkylarylsulphonates. Quaternary ammonium salts of formula (II) which are preferred, on the one hand, are tetraalkylammonium chlorides such as, for example, dialkyldimethylammonium or alkyltrimethylammonium chlorides, in which the alkyl radical contains from 12 to 22 carbon atoms approximately, in particular behenyltrimethylammonium chloride, distearyldimethylammonium chloride, cetyltrimethylammonium chloride or benzyldimethylstearylammonium chloride, or alternatively, on the other hand, stearamidopropyl-dimethyl(myristyl acetate)ammonium chloride sold under the name Ceraphyl 70 by Van Dyk.

quaternary ammonium salts of imidazolinium, such as, for example, those of formula (III) below:

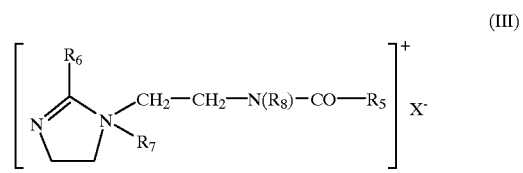

(III)

in which $R_5$ represents an alkenyl or alkyl radical containing from 8 to 30 carbon atoms, for example a tallow fatty acid derivative; $R_6$ represents a hydrogen atom, an alkyl radical containing from 1 to 4 carbon atoms or an alkenyl or alkyl radical containing from 8 to 30 carbon atoms; $R_7$ represents an alkyl radical containing from 1 to 4 carbon atoms; $R_8$ represents a hydrogen atom or an alkyl radical containing from 1 to 4 carbon atoms; X is an anion selected from the group formed by halides, phosphates, acetates, lactates, alkyl sulfates and alkyl or alkylarylsulphonates. Preferably, $R_5$ and $R_6$ denote a mixture of alkenyl or alkyl radicals containing from 12 to 21 carbon atoms, for example tallow fatty acid derivatives, $R_7$ denotes a methyl radical and $R_8$ denotes hydrogen. Such a product is sold, for example, under the name Rewoquat W75 by Rewo.

diquaternary ammonium salts of formula (IV):

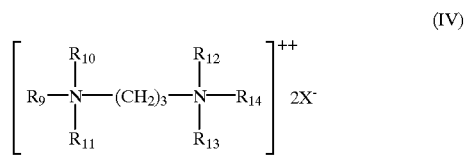

(IV)

in which $R_6$ denotes an aliphatic radical containing from 16 to 30 carbon atoms approximately; $R_7$, $R_8$, $R_9$, $R_{10}$ and $R_{11}$, are selected from hydrogen and an alkyl radical containing from 1 to 4 carbon atoms; and X is an anion selected from the group formed by halides, acetates, phosphates, nitrates and methyl sulfates. Such diquaternary ammonium salts in particular comprise propane tallow diammonium dichloride. When the ionic surfactant(s) is/are present, it/they can be present in an amount of not more than 20% by weight relative to the weight of nonionic surfactant(s) used. When the composition contains ionic surfactant(s), the amount thereof preferably ranges from 0.01 to 5% by weight relative to the total weight of the surfactant system.

In addition, in the composition of the invention, the amount of the surfactant system preferably ranges from 0.1% to 4.25% and better still from 0.5% to 3% by weight relative to the total weight of the composition. This range includes all specific values and subranges therebetween, such as 0.2, 1.0, 1.5, 2.0, 2.5 and 3.5% by weight relative to the total weight of the composition.

The glycerol phase/surfactant system weight ratio is advantageously greater than or equal to 20 and preferably ranges from 20 to 50. This range includes all specific values and subranges therebetween, such as 25, 30, 35, 40 and 45.

The glycerol phase contains at least glycerol. In one preferred embodiment of the invention, it also contains at least one glycol. Such a combination allows the long-term stability of the emulsion to be improved.

The glycols used in the composition of the invention can be selected, for example, from propylene glycol, 1,3- butylene glycol, dipropylene glycol, pentylene glycol, isoprene glycol and polyethylene glycols, in particular those comprising 4 to 16 ethylene oxide units and preferably from 8 to 12 ethylene oxide units, and mixtures thereof.

The glycerol phase represents, in the composition of the invention, at least 30% by weight relative to the total weight of the composition, preferably from 30% to 85% and better still from 40% to 75% by weight relative to the total weight of the composition. According to one preferred embodiment of the invention, the glycerol and the optional glycol(s) are present in a glycerol/glycols weight ratio ranging from 0.5 to 5 and preferably from 1 to 5.

It is possible to introduce water into the emulsion of the invention. Preferably, the amount of water is such that the water activity (aw) of the final composition is not greater than 0.7. Various methods can be used to measure the water activity of a composition, the most common being the manometric method by which vapor pressure is measured directly. Preferably, the amount of water in the composition of the invention is not more than 20% by weight relative to the total weight of the composition.

The oily phase of the composition according to the invention generally represents from 5 to 45% and preferably from 15 to 35% by weight relative to the total weight of the composition. These ranges include all specific values and subranges therebetween, such as 10, 20, 25, 30 and 40% by weight relative to the total weight the composition.

The nature of the oily phase in the emulsion according to the invention is not critical. The oily phase can thus consist of any fatty substance, and in particular oils, usually used in cosmetics or dermatology.

Among the oils which can be used in the emulsion of the invention, mention may be made, for example, of oils of plant origin, such as jojoba oil, avocado oil, sweet almond oil, apricot oil, corn oil and the liquid fraction of karite butter; mineral oils such as liquid petroleum jelly; synthetic oils such as triglycerides (for example caprylic/capric triglycerides), 2-ethylhexyl palmitate, isopropyl myristate, hydrogenated isoparaffin, isononyl isononanoate or cetearyl octanoate; volatile or non-volatile silicone oils, and fluoro oils. The other fatty substances which may be present in the oily phase can be, for example, fatty acids, fatty alcohols, waxes and lipids such as ceramides.

The composition according to the invention can in particular constitute a cosmetic or dermatological composition and, in this case, contains a physiologically acceptable medium, i.e. a medium which is compatible with the skin, the lips, the scalp, the eyes and/or the hair.

In a known manner, the compositions of the invention can contain adjuvants that are common in the fields under consideration, such as hydrophilic and/or lipophilic active agents (for example tocopherol and its derivatives such as tocopheryl acetate; retinol and its esters such as retinyl palmitate; flavonoids or plant extracts containing them; etc.), preserving agents, antioxidants, fragrances, solvents, fillers, screening agents, dyestuffs, basic or acidic agents and lipid vesicles. These adjuvants are used in the usual proportions in the fields under consideration, and, for example, from 0.01 to 30% relative to the total weight of the composition, and, depending on their nature, they are introduced into either phase of the emulsion, or alternatively into vesicles. These adjuvants and the concentrations thereof should be such that they do not modify the desired property for the emulsion of the invention.

The addition of fillers makes it possible, if need be, to modify the texture of the composition. As fillers which can be used in the composition of the invention, mention may be made, for example, besides pigments, of silica powder; talc; polyamide particles and in particular those sold under the name Orgasol by Atochem; polyethylene powders; microspheres based on acrylic copolymers, such as those made of ethylene glycol dimethacrylate/lauryl methacrylate copolymer, sold by Dow Coming under the name Polytrap; expanded powders such as hollow microspheres and in particular the microspheres sold under the name Expancel by Kemanord Plast or under the name Micropearl F 80 ED by Matsumoto; powders of natural organic materials such as crosslinked or non-crosslinked cornstarch, wheatstarch or rice starch, such as the powders of starch crosslinked with octenylsuccinate anhydride, sold under the name Dry-Flo by National Starch; silicone resin microbeads such as those sold under the name Tospearl by Toshiba Silicone; and mixtures thereof. These fillers can be present in an amount ranging from 0 to 10% by weight and preferably from 0.5 to 4% by weight relative to the total weight of the composition.

The surfactant system used in the composition of the invention allows a stable emulsion to be obtained. However, depending on the amount and nature of the surfactant, it may be necessary to correct the variations in viscosity by introducing gelling agents. Thus, it is possible to introduce a hydrophilic or lipophilic gelling agent into the composition of the invention, provided that it is capable of swelling in the phase in which it is dispersed. Hydrophilic gelling agents which may be mentioned in particular are carboxyvinyl polymers (carbomer), acrylic copolymers such as acrylate/alkylacrylate copolymers, polyacrylamides, polysaccharides, natural gums, DNA and clays, and lipophilic gelling agents which may be mentioned are modified clays such as bentones, metal salts of fatty acids, hydrophobic silica and polyethylenes.

The compositions according to the invention are opalescent to opaque and may be more or less fluid. They can thus be in the form of a serum, a milk, a cream or a paste. These compositions are prepared according to the usual methods.

The compositions which are the subject of the invention find their application in particular in a large number of cosmetic treatments for the skin, the lips and the hair, including the scalp, in particular for treating, protecting, caring for, removing make-up from and/or cleansing the skin, the lips and/or the hair, and/or for making up the skin and/or the lips.

Thus, a subject of the invention is also the cosmetic use of the composition as defined above for toning the skin and/or for smoothing out wrinkles and fine lines on the skin and/or for combating the harmful effects of WV radiation and pollution and/or for depigmenting the skin.

A subject of the invention is also a cosmetic treatment process for the skin, characterized in that a composition as defined above is applied to the skin.

A subject of the invention is also the use of the composition as defined above for the manufacture of a preparation intended to tone the skin and/or to smooth out wrinkles and fine lines on the skin and/or to combat the harmful effects of UV radiation and pollution and/or to depigment the skin.

A subject of the invention is also a process for stabilizing an oxidation-sensitive hydrophilic compound, comprising the steps consisting in:

(a) introducing, into glycerol to which glycol(s) and/or water has (have) optionally been added, a surfactant capable of forming a lamellar phase on contact with glycerol and having a melting point of at least 35° C., (b) adding the said hydrophilic compound to the above mixture, (c) incorporating at least one oil into the mixture thus obtained, in order to form an emulsion, and (d) subjecting the resulting emulsion to high-speed homogenization, at a temperature about 5° C. above the phase transition temperature of the said surfactant.

EXAMPLES

The examples which follow will allow the invention to be understood more clearly without, however, being limiting in nature. Except where otherwise mentioned, the amounts indicated are percentages by weight.

Example 1

| Organogel | |
|---|---|
| Hydrogenated lecithin (Emulmetik 950 from Lucas Meyer) | 2% |
| Glycerol Phase | |
| Glycerol | 45% |
| Dipropylene glycol | 15% |
| Ascorbic acid | 10% |
| Oily Phase | |
| Apricot kernel oil | 27% |
| Tocopheryl acetate | 1% |

Procedure: The hydrogenated lecithin is introduced with vigorous stirring at 75° C. into the mixture of glycerol and dipropylene glycol. Stirring is maintained under these conditions for 30 minutes. The ascorbic acid is then introduced at between 70° C. and 65° C. and stirring is continued until it has fully dissolved. The oily phase is then added, still under the same conditions which are maintained for a further one hour. The heating is then stopped and the stirring speed is reduced until the temperature has fallen to 60° C. The mixture is then blended in a high-speed rotor-stator homogenizer (Ultra-Turrax) at about 20,000 rpm for 2 minutes and at a temperature about 5° C. above the phase transition temperature of the surfactant in the glycerol phase, which for hydrogenated lecithin is between 50° C. and 55° C. The lamellar network forms within 24 hours.

A very fine fluid gel is obtained. Its water activity value aw is 0.1445. The fluid is stable for two months at 4° C., 25° C., 37° C. and 45° C., i.e., no creaming, sedimentation or phase-separation of the emulsion is observed. In addition, an HPLC assay of the ascorbic acid shows a loss of only 5% ascorbic acid after storage for two months at 45° C., although no specific precautions were taken during the preparation or storage of the fluid.

This fluid can be used in particular for skin care, in order to prevent and/or combat the signs of ageing.

Example 2

| Organogel | |
|---|---|
| Triglyceryl distearate (Emalex DGS 3 from the company Nikko) | |
| Glycerol Phase | |
| Glycerol | 2% |
| Dipropylene glycol | 47% |
| Ascorbic acid | 18% |
| glycerol phase | 5% |

| Organogel | |
|---|---|
| Oily Phase | |
| Apricot kernel oil | 27% |
| Tocopheryl acetate | 1% |

This composition is prepared in the same way as in Example 1, except that the blending temperature in the high-speed homogenizer is between 45° C. and 55° C.

A very fine fluid gel is obtained. Its water activity value a w is 0.1. The fluid is stable for two months at 4° C., 25° C., 37° C. and 45° C., i.e., no creaming, sedimentation or phase-separation of the emulsion is observed. In addition, an HPLC assay of the ascorbic acid shows a loss of only 3.6% ascorbic acid after storage for two months at 45° C., although no specific precautions were taken during the preparation or storage of the fluid.

This fluid can be used in particular for skin care, in order to prevent and/or combat environmental attacking factors, in particular UV and pollution.

Example 3

| Organogel | |
|---|---|
| Hydrogenated lecithin (Emulmetik 950 from Lucas Meyer) | 2% |
| Glycerol Phase | |
| Glycerol | 36% |
| Dipropylene glycol | 14% |
| Ascorbic acid | 10% |
| Oily Phase | |
| Apricot kernel oil | 27% |
| Tocopheryl acetate | 1% |
| Plant DNA gel at 0.5% in water | 10% |

The procedure is identical to that of Example 1, except that the DNA gel is added at 55° C. with stirring, after homogenization in the high-speed rotor-stator. Once the gel has been dispersed, the stirring is stopped until the mixture has cooled to room temperature.

A slightly runny, opalescent and fine organogel is obtained, which is fully stable for two months at 4° C., 25° C., 37° C. and 45° C., i.e., no creaming, sedimentation or phase-separation of the emulsion is observed. In addition, an HPLC assay of the ascorbic acid shows a loss of only 10% ascorbic acid after storage for two months at 45° C., although no specific precautions were taken during the preparation or storage of the fluid.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-11117, filed on Sept. 6, 1999, and incorporated herein by reference in its entirety.

What is claimed is:

1. An emulsion comprising:
a glycerol phase containing an oxidation-sensitive hydrophilic compound selected from the group consisting of ascorbic acid, hydrophilic derivatives thereof, and enzymes. an oily phase dispersed in the glycerol phase; and at least one surfactant in a lamellar phase and having a melting point of greater than or equal to 35° C.

2. The emulsion of claim 1, wherein the surfactant is a nonionic surfactant selected from the group consisting of hydrogenated lecithin enriched with phosphatidylcholine, fatty esters of polyols, fatty ethers of polyols, mixtures of fatty esters of polyols and mixtures of fatty ethers of polyols.

3. The emulsion of claim 2, wherein the fatty ester of polyol is formed from at least one polyol and from at least one fatty acid containing from 8 to 22 carbon atoms and having a saturated or unsaturated, linear or branched chain.

4. The emulsion of claim 2, wherein the fatty acid is selected from palmitic acid and stearic acid, and mixtures thereof.

5. The emulsion of claim 2, wherein the fatty ether of polyol is formed from at least one polyol and from at least one fatty alcohol containing from 8 to 22 carbon atoms and having a saturated or unsaturated, linear or branched chain.

6. The emulsion of claim 2, wherein the fatty alcohol is selected from cetyl alcohol, stearyl alcohol and lauryl alcohol, and mixtures thereof.

7. The emulsion of claim 2, wherein the fatty ester of polyol or the fatty ether of polyol are formed from a polyol selected from the group consisting of glycerol, polyglycerols, sorbitan, polysorbitans, polyoxyethylenated sorbitan derivatives, polyethylenes, sucrose, glucose, oxyethylenated glucose derivatives, polyglucoses and oxyethylenated polyglucoses, and mixtures thereof.

8. The emulsion of claim 2, wherein said surfactant is selected from the group consisting of polyoxyethylenated derivatives of cetyl, stearyl and/or lauryl alcohol, esters of sorbitan and of stearic acid, esters of sorbitan and of palmitic acid, esters of sucrose and of stearic acid, esters of polyethylene glycol and of stearic acid, esters of glycerol or of polyglycerol and of stearic acid, and mixtures thereof.

9. The emulsion of claim 1, further comprising at least one additive selected from the group consisting of sterols, long-chain alcohols, long chain diols, long-chain amines and quaternary ammonium derivatives thereof.

10. The emulsion of claim 1, wherein said surfactant is an ionic surfactant.

11. The emulsion of claim 1, wherein the amount of the surfactant ranges from 0.1% to 4.25% by weight relative to the total weight of the emulsion.

12. The emulsion of claim 1, wherein the glycerol phase also contains at least one glycol.

13. The emulsion of claim 12, wherein the glycol is selected from the group consisting of propylene glycol, 1,3-butylene glycol, dipropylene glycol, pentylene glycol, isoprene glycol and polyethylene glycols, and mixtures thereof.

14. The emulsion of claim 12, wherein the glycerolglycol (s) weight ratio ranges from 0.5 to 5.

15. The emulsion of claim 1, wherein the glycerol phase represents at least 30% by weight relative to the total weight of the emulsion.

16. The emulsion of claim 1, further comprising water.

17. The emulsion of claim 1, further comprising a gelling agent.

18. The emulsion of claim 1, wherein the oily phase represents from 5% to 45% by weight relative to the total weight of the composition.

19. A method of toning the skin and/or smoothing out wrinkles and fine lines on the skin and/or combatting the harmful effects of UV radiation and pollution and/or depigmenting the skin, comprising applying the emulsion of claim 1 to the skin.

20. A method of cosmetically treating skin, comprising applying the emulsion of claim 1 to the skin.

21. A method of stabilizing an oxidation-sensitive hydrophilic compound, comprising:
  (a) introducing, into glycerol to which glycol(s) and/or water has (have) optionally been added, a surfactant capable of forming a lamellar phase on contact with glycerol and having a melting point of at least 35° C.,
  (b) adding the hydrophilic compound to the above mixture,
  (c) incorporating at least one oil into the mixture thus obtained, to produce an emulsion, and
  (d) subjecting the resulting emulsion to high-speed homogenization, at a temperature about 5° C. above the phase transition temperature of the surfactant.

22. An emulsion obtained by the process of claim 21.

23. A method of making the emulsion of claim 1, comprising:
  combining said glycerol and said surfactant;
  adding said hydrophilic compound to the combined glycerol and surfactant; and then adding at least one oil.

24. The emulsion of claim 1, wherein said surfactant comprises ionic surfactant(s) and nonionic surfactant(s).

25. The emulsion of claim 24, wherein the amount of ionic surfactant(s) is not more than 20% by weight relative to the weight of nonionic surfactant(s) in a lamellar phase.

26. The emulsion of claim wherein said glycerol phase represents from 30% to 85% by weight relative to the total weight of the emulsion.

27. The emulsion of claim 1, wherein said surfactant is amphiphilic, insoluble in water and has an HLB of 2 to 8.

28. The emulsion claimed in claim 1 wherein the oxidation-sensitive hydrophilic compound is ascorbic acid.

29. The emulsion claimed in claim 1 wherein the oxidation-sensitive hydrophilic compound is an enzyme.

30. The emulsion claimed in claim 1 wherein the oxidation-sensitive hydrophilic compound is an enzyme selected from the group consisting of lactoperoxidase, lipase, protease, phospholipase, cellulase, catalase, and superoxide dismutase.

* * * * *

UNITED STATES PATENT AND TRADEMARK OFFICE
CERTIFICATE OF CORRECTION

PATENT NO.    : 6,342,238 B1
DATED         : January 29, 2002
INVENTOR(S)   : Jean-Thierry Simonnet et al.

It is certified that error appears in the above-identified patent and that said Letters Patent is hereby corrected as shown below:

<u>Column 10,</u>
Line 66, delete "." and insert -- ; --;
Line 66, the phrase "an oily phase dispersed in the glycerol phase; and" should be located on the next line (67).

<u>Column 11,</u>
Line 53, delete "glycerolglycol" and insert -- glycerol/glycol(s) --.

<u>Column 12,</u>
Lines 50-54, should read -- The emulsion claimed in claim 1 wherein at least one enzyme is selected from the group consisting of lactoperoxidase, lipase, protease, phospholipase, cellulase, catalase, and superoxide dismutase. --;

Signed and Sealed this

Twelfth Day of August, 2003

JAMES E. ROGAN
*Director of the United States Patent and Trademark Office*